(12) United States Patent     (10) Patent No.: US 11,052,213 B2
Romano     (45) Date of Patent: Jul. 6, 2021

(54) OXYGEN DELIVERY SYSTEM FOR PROVIDING CONTROLLED FLOW OF OXYGEN-ENRICHED GAS TO A PATIENT

(71) Applicant: KONINKLIJKE PHILIPS N.V., Eindhoven (NL)

(72) Inventor: Robert Romano, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 313 days.

(21) Appl. No.: 16/210,924

(22) Filed: Dec. 5, 2018

(65) Prior Publication Data

US 2019/0175864 A1     Jun. 13, 2019

Related U.S. Application Data

(60) Provisional application No. 62/598,195, filed on Dec. 13, 2017.

(51) Int. Cl.
*A61M 16/10*     (2006.01)
*A61B 5/11*     (2006.01)
(Continued)

(52) U.S. Cl.
CPC ....... *A61M 16/101* (2014.02); *A61B 5/02416* (2013.01); *A61B 5/0833* (2013.01);
(Continued)

(58) Field of Classification Search
CPC ........ A61M 16/10–101; A61M 2016/102–103
See application file for complete search history.

(56) References Cited

U.S. PATENT DOCUMENTS

| 4,211,239 A | 7/1980 | Raemer |
| 6,244,540 B1 * | 6/2001 | Stabile ..................... A62B 7/14 244/118.5 |

(Continued)

FOREIGN PATENT DOCUMENTS

| EP | 1972356 A1 | 9/2008 |
| WO | 2007072239 A2 | 6/2007 |

OTHER PUBLICATIONS

Smolander et al: "A New Heart Rate Variability-Based Method for the Estimation of Oxygen Consumption without Individual Laboratory Calibration: Application Example on Postal Workers", Applied Ergonomics, Butterworth Scientific Ltd, Guildford, GB, vol. 39, No. 3, Oct. 24, 2007 (Oct. 24, 2007), pp. 325-331, XP022425334.

(Continued)

*Primary Examiner* — Rachel T Sippel
(74) *Attorney, Agent, or Firm* — Daniel H. Brean

(57) ABSTRACT

An oxygen delivery system provides controlled flow of oxygen-enriched gas to a patient. The system includes one or more sensors configured to measure respiration rate information and heart rate information of the patient. A computer system including one or more physical processors is operatively connected with the sensors. The physical processors are programmed with computer program instructions which, when executed cause the computer system to determine a metabolic oxygen consumption information of the patient from the respiration rate information and the heart rate information from the one or more sensors, and continuously adjust flow, volume and/or pressure of the oxygen-enriched gas delivered from an oxygen source of the oxygen delivery system to the patient based on the determined metabolic oxygen consumption information of the patient.

20 Claims, 4 Drawing Sheets

(51) Int. Cl.
*A61M 16/06* (2006.01)
*A61M 16/00* (2006.01)
*A61B 5/024* (2006.01)
*A61B 5/083* (2006.01)
*A61B 5/00* (2006.01)
*A61M 16/20* (2006.01)

(52) U.S. Cl.
CPC .......... *A61B 5/1102* (2013.01); *A61B 5/4836* (2013.01); *A61M 16/024* (2017.08); *A61M 16/0666* (2013.01); *A61M 16/1005* (2014.02); *A61M 16/202* (2014.02); *A61B 5/681* (2013.01); *A61M 2016/0027* (2013.01); *A61M 2016/1025* (2013.01); *A61M 2202/0208* (2013.01); *A61M 2205/3306* (2013.01); *A61M 2205/3331* (2013.01); *A61M 2205/3584* (2013.01); *A61M 2205/3592* (2013.01); *A61M 2205/52* (2013.01); *A61M 2230/04* (2013.01); *A61M 2230/06* (2013.01); *A61M 2230/205* (2013.01); *A61M 2230/42* (2013.01); *A61M 2230/63* (2013.01)

(56) References Cited

U.S. PATENT DOCUMENTS

| | | | |
|---|---|---|---|
| 6,651,658 B1 | 11/2003 | Hill | |
| 7,617,826 B1* | 11/2009 | Voege | A61M 16/20 |
| | | | 128/204.26 |
| 9,440,036 B2 | 9/2016 | Wilkinson | |
| 2003/0159696 A1* | 8/2003 | Boussignac | A61M 16/127 |
| | | | 128/204.24 |
| 2006/0241506 A1* | 10/2006 | Melker | A61B 5/411 |
| | | | 600/529 |
| 2008/0230065 A1* | 9/2008 | Heinonen | A61M 16/0051 |
| | | | 128/204.23 |
| 2009/0173348 A1 | 7/2009 | Fisher | |
| 2013/0125891 A1 | 5/2013 | Eddy | |
| 2014/0123979 A1* | 5/2014 | Doyle | A61M 16/04 |
| | | | 128/204.23 |
| 2015/0080669 A1 | 3/2015 | Settels | |
| 2015/0083121 A1 | 3/2015 | Fisher | |
| 2016/0174903 A1 | 6/2016 | Cutaia | |
| 2016/0235309 A1 | 8/2016 | Olivier | |
| 2016/0375215 A1 | 12/2016 | Wilkinson | |
| 2017/0113013 A1 | 4/2017 | Allum | |
| 2019/0125999 A1* | 5/2019 | Haussermann | A61M 16/10 |
| 2019/0201644 A1* | 7/2019 | Hallback | A61B 5/082 |
| 2020/0085357 A1* | 3/2020 | Kuenen | A61B 5/682 |

OTHER PUBLICATIONS

Winck, João Carlos, "Intelligent oxygen delivery in the acute setting: Don't think twice, it's all right"; European Respiratory Journal, 2017, 50: 1701013; DOI: 10.1183/13993003.01013.

Smolander, J. et al, "A New Heart Rate Variability-based Method for the Estimation of Oxygen Consumption without Individual Laboraotry Calibration: Application example of postal Workers", Applied Ergonomics, May 2008. vol. 39, No. 3, pp. 325-331.

"Energy Expenditure Estimation Method based on Heart Rate Measurement", Firstbeat Technologies Ltd. Feb. 2007.

Junnila, S. et al "An EMFi-film Sensor based Ballistocardiographic Chair Performance and Sycle Extraction Method", IEEE Workshop on Signal Processing Systems Design and Implementation, Nov. 2005, pp. 373-377.

Harland, C.J. et al "High Resolution Ambulatory Electrocardiographic Monitoring using Wrist-Mounted Electric Potential Sensors", Meas. Sci. Techol., vol. 14, No. 7, 2003, pp. 923-928.

Brink, M. et al "Contact-Free Measurement of Heart Rate, Respiration Rate, and body movements during Sleep", Behavior Research Methods, 2006, vol. 38, No. 3, pp. 511-521.

Morbiducci, U. et al "Optical Vibrocardiography: A Novel Tool for the Optical Monitoring of Cardiac Activity", Annals of Biomedical Engineering, vol. 35, No. 1, pp. 45-58, Jan. 2007.

* cited by examiner

OXYGEN DELIVERY SYSTEM FOR PROVIDING CONTROLLED FLOW OF OXYGEN-ENRICHED GAS TO A PATIENT

CROSS-REFERENCE TO RELATED APPLICATIONS

This patent application claims the priority benefit under 35 U.S.C. § 119(e) of U.S. Provisional Application No. 62/598,195, filed on Dec. 13, 2017, the contents of which are herein incorporated by reference.

BACKGROUND OF THE INVENTION

1. Field of the Invention

The present patent application discloses an oxygen delivery system for providing controlled flow of oxygen-enriched gas to a patient.

2. Description of the Related Art

A growing number of people in the United States suffer from chronic obstructive pulmonary disease (COPD) such as asthma and emphysema, as well as cystic fibrosis, lung cancer, lung injuries, cardiovascular diseases, and otherwise diseased or damaged lungs. Although there is no cure for many of these conditions, their detrimental impact of can be mitigated by the prescription of oxygen therapy. The inhalation of oxygen-enriched gas serves to compensate for the poor function of the patient's lungs in absorbing oxygen. More and more people are using oxygen therapy outside the hospital, permitting them to lead active, productive lives. Recent developments in oxygen therapy technology have given those dependent upon oxygen a variety of in-home and portable options for oxygen therapy.

U.S. Patent Application Publication No. 2013/0125891 discloses a closed loop oxygen delivery system based on oxygen saturation ($SpO_2$) derived from pulse oximeters. However, oxygen saturation derived from pulse oximeters only reflects the amount of oxygen present in the arterial system without the ability to anticipate the level of oxygen that will be utilized by the patient. In some situations or disease states, even though oxygen content ($SpO_2$) derived from pulse oximeters may be normal, oxygen delivery can be impaired and oxygen extraction can increase, creating an even larger demand for oxygen delivery.

Also, it has been found that pulse oximeters must rely on sufficient perfusion at the sensor site or location and may suffer inaccuracies or data drop-out when there is motion or movement artifact, likely to occur during patient exertion when the proper adjustment of oxygen is even more critical.

Therefore, an improved oxygen delivery system for providing controlled flow of oxygen-enriched gas is needed.

SUMMARY OF THE INVENTION

Accordingly, it is an object of one or more embodiments of the present patent application to provide an oxygen delivery system for providing controlled flow of oxygen-enriched gas to a patient. The system comprises one or more sensors and a computer system. The one or more sensors for measuring respiration rate information of the patient and heart rate information of the patient. The computer system comprises one or more physical processors operatively connected with the one or more sensors. The one or more physical processors are programmed with computer program instructions which, when executed cause the computer system to determine a metabolic oxygen consumption information of the patient from the respiration rate information of the patient and the heart rate information of the patient from the one or more sensors, and continuously adjust flow, volume and/or pressure of the oxygen-enriched gas delivered from an oxygen source of the oxygen delivery system to the patient based on the determined metabolic oxygen consumption information of the patient.

It is yet another aspect of one or more embodiments of the present patent application to provide a method for providing controlled flow of oxygen-enriched gas from an oxygen delivery system to a patient. The method is implemented by a computer system that comprises one or more physical processors operatively connected with one or more sensors and executing computer program instructions which, when executed, perform the method. The method comprises obtaining, from the one or more sensors, respiration rate information of the patient and heart rate information of the patient; determining, by the computer system, a metabolic oxygen consumption information of the patient from the respiration rate information of the patient and the heart rate information of the patient; and continuously adjusting, by the computer system, flow, volume and/or pressure of the oxygen-enriched gas delivered from an oxygen source of the oxygen delivery system to the patient based on the determined metabolic oxygen consumption information of the patient.

It is yet another aspect of one or more embodiments to provide a system for providing controlled flow of oxygen-enriched gas from an oxygen delivery system to a patient. The system comprises a means for executing machine-readable instructions with at least one processor. The machine-readable instructions comprises obtaining, from one or more sensors, respiration rate information of the patient and heart rate information of the patient; determining a metabolic oxygen consumption information of the patient from the respiration rate information of the patient and the heart rate information of the patient; and continuously adjusting, by the computer system, flow, volume and/or pressure of the oxygen-enriched gas delivered from an oxygen source of the oxygen delivery system to the patient based on the determined metabolic oxygen consumption information of the patient.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1A:
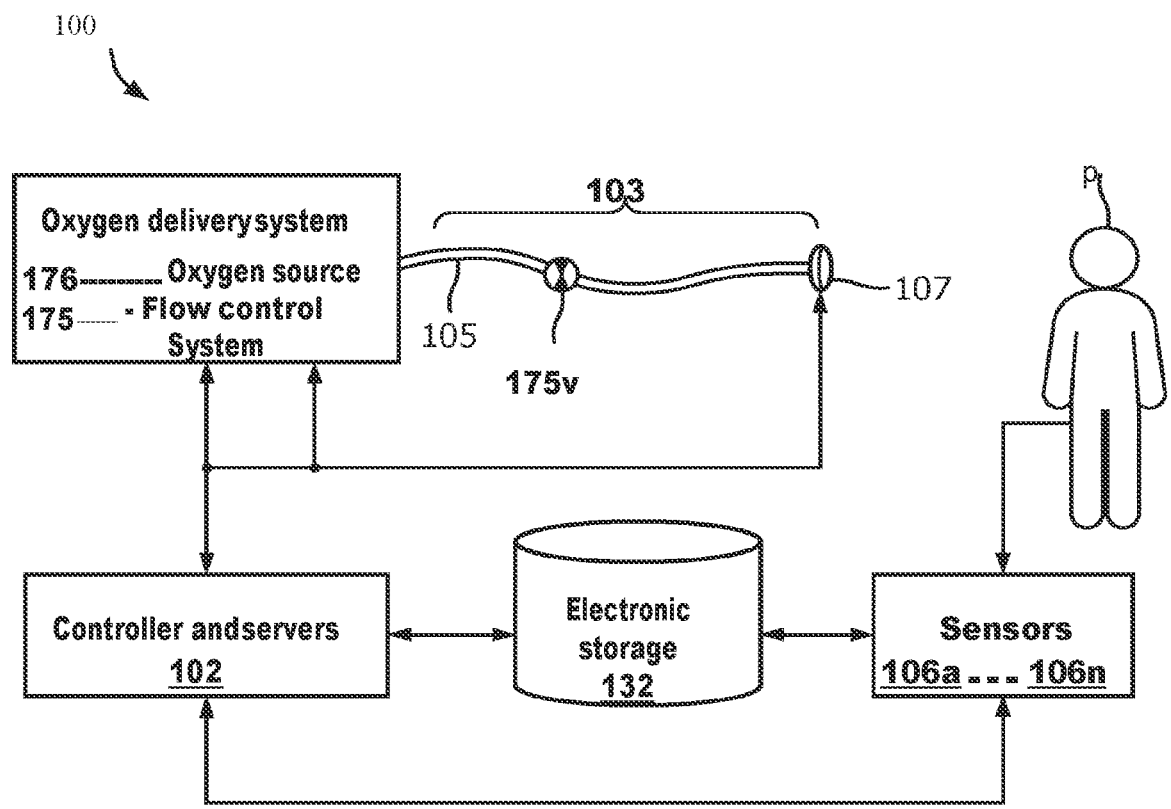
FIG. 1A illustrates an exemplary oxygen delivery system for providing controlled flow of oxygen-enriched gas to a patient in accordance with an embodiment of the present patent application.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1B:
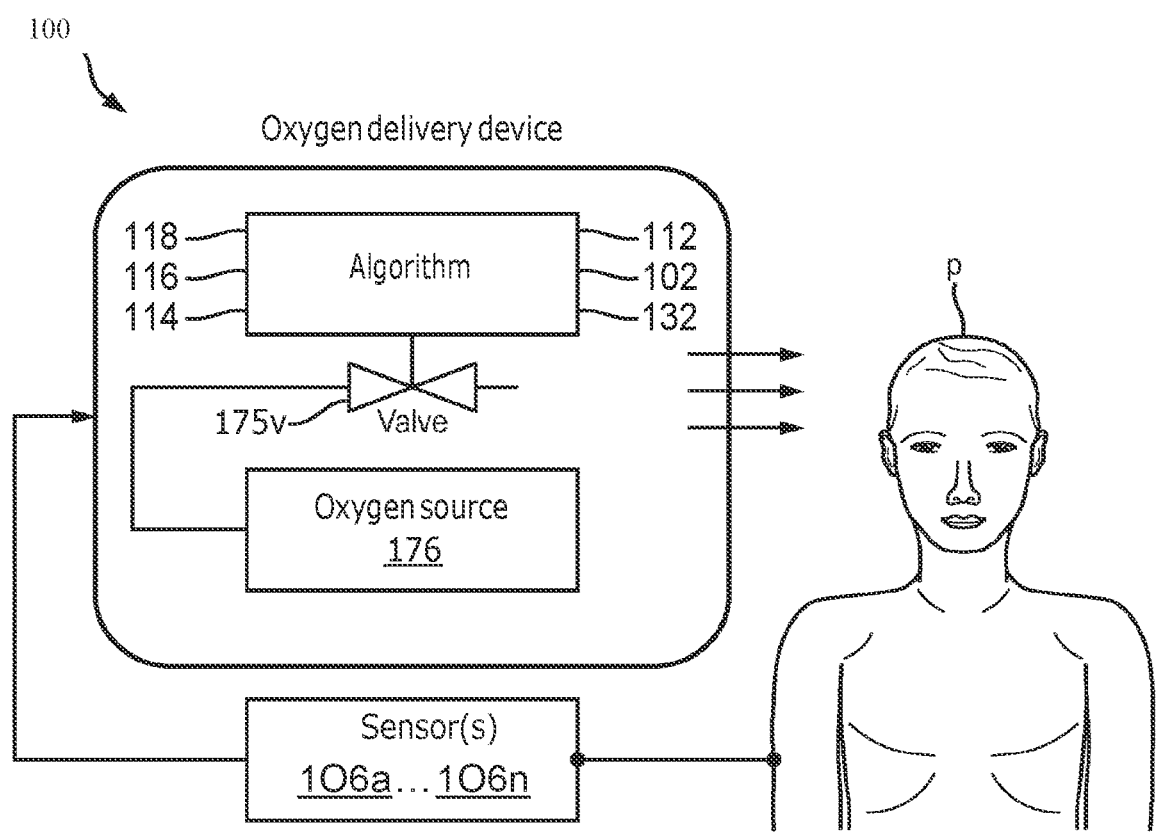
FIG. 1B illustrates an exemplary oxygen delivery system for providing controlled flow of oxygen-enriched gas to a patient in accordance with an embodiment of the present patent application.
Figure 2:
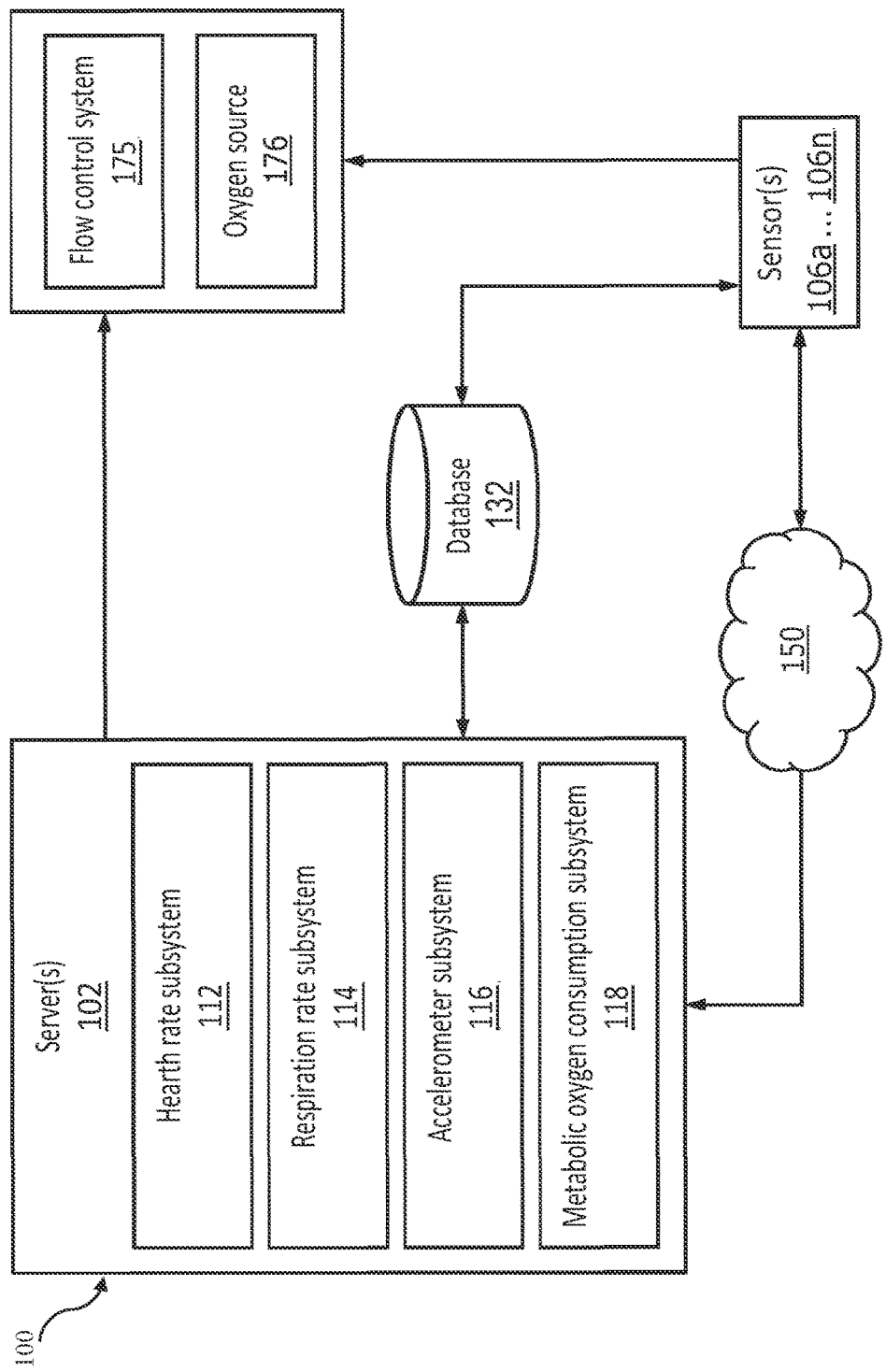
FIG. 2 illustrates another exemplary oxygen delivery system for providing controlled flow of oxygen-enriched gas to a patient in accordance with an embodiment of the present patent application.

FIGS. 1A, 1B and 2 show system 100 for providing controlled flow of oxygen-enriched gas to a patient P, in accordance with one or more embodiments. For example, FIGS. 1A and 1B are high level views of system 100.

Oxygen delivery system 100 comprises one or more sensors 106a . . . 106n and a computer system 102. One or more sensors 106a . . . 106n are configured for measuring respiration rate information of the patient and heart rate information of the patient. In one embodiment, computer system 102 comprises one or more physical processors operatively connected with one or more sensors 106a . . . 106n. The one or more physical processors are programmed with computer program instructions which, when executed cause computer system 102 to determine a metabolic oxygen consumption information of the patient from the respiration rate information of the patient and the heart rate information of the patient from one or more sensors 106a . . . 106n, and continuously adjust flow, volume and/or pressure of the oxygen-enriched gas delivered from an oxygen source 176 of oxygen delivery system 100 to the patient based on the determined metabolic oxygen consumption information of the patient. In one embodiment, a person's or patient's metabolic oxygen consumption (VO2) is the amount of oxygen taken up and utilized by the person's or patient's body per minute. In one embodiment, in VO2, V refers to volume and O2 refers to oxygen. In one embodiment, V in VO2 represents not just a volume, but a volume rate (i.e., a volume per unit of time). In one embodiment, metabolic rate of the patient may directly relate with oxygen consumption. In one embodiment, patient's metabolic oxygen consumption VO2 is measured in milliliters per kilogram of body weight per minute (ml/kg/min). In one embodiment, patient's metabolic oxygen consumption is an estimated metabolic oxygen consumption or a derived patient's metabolic oxygen consumption. In one embodiment, patient's metabolic oxygen consumption of the present patent application is not the actual oxygen consumption.

In one embodiment, patient's metabolic oxygen consumption $VO_2$ is a measure of the volume of oxygen that is used by the patient to convert the energy from the food you eat into the energy molecules, called adenosine triphosphate (ATP), that patient uses at the cellular level. That is, in one embodiment, the oxygen taken into the patient's body at the level of the lungs is ultimately transported by the cardiovascular system of the patient to the systemic tissues and is used for the production of adenosine triphosphate (ATP) in the mitochondria of the patient's cells.

In one embodiment, metabolic oxygen consumption $VO_2$ is dependent on the ability of the heart to pump out blood, the ability of the tissues to extract oxygen from the blood, the ability of the lungs to ventilate and the ability of the alveoli to extract oxygen from the air. In one embodiment, metabolic oxygen consumption $VO_2$ may be estimated by or determined from heart rate information of the patient, and respiration rate information of the patient. In one embodiment, metabolic oxygen consumption $VO_2$ may be estimated by or determined from heart rate information of the patient, respiration rate information of the patient and accelerometer information of the patient. In one embodiment, the solution provided by the present patent application is device agnostic. In one embodiment, as described in detail below, the data or information collected may be from any sensor(s) and derived by any number of means. In one embodiment, this data or information may then be fed into an oxygen/gas controller where the flow of oxygen-air admixture is automatically adjusted accordingly.

In one embodiment, metabolic oxygen consumption $VO_2$ is estimated by or determined from heart rate information of the patient, respiration rate information of the patient and/or accelerometer information of the patient using a Bayesian network or model.

In another embodiment, metabolic oxygen consumption $VO_2$ is estimated by or determined from heart rate information of the patient, respiration rate information of the patient and/or accelerometer information of the patient using a Neural network.

In one embodiment, for example, metabolic oxygen consumption $VO_2$ is estimated by or determined from heart rate information of the patient, respiration rate information of the patient and/or accelerometer information of the patient using the methods disclosed in "A new heart rate variability-based method for the estimation of oxygen consumption without individual laboratory calibration: Application example on postal Workers," by Smolander J, Juuti T, Kinnunen ML, Laine K, Louhevaara V, Männikkö K, Rusko H., in Applied Ergonomics. May 2008; 39(3):325-31. Epub 2007 Oct. 24 and "Energy Expenditure Estimation Method Based on Heart Rate Measurement," by Firstbeat Technologies Ltd. and published: February 2007, both are herein incorporated by reference in their entirety into the present patent application.

In one embodiment, oxygen delivery system 100 is a prescription oxygen delivery device. In one embodiment, oxygen delivery system 100 includes a bottled gas or portable oxygen concentrators. In one embodiment, the oxygen therapies or modes of providing oxygen to the patient are implemented by any suitable oxygen delivery system that is capable of controlling the flow of oxygen delivered to the patient in a feedback fashion. In one embodiment, oxygen delivery system 100 can be any system that delivers an oxygen/air gas admixture to the patient.

In one embodiment, oxygen delivery system 100 generally includes source of oxygen 176, such as an oxygen concentrator, a pressurized supply of gaseous oxygen contained in a pressurized vessel, or a supply of liquid oxygen. In one embodiment, oxygen source 176 can be from an oxygen bottle or oxygen concentrator, as examples. In one embodiment, an oxygen concentrator is used to generate oxygen from ambient air. In on embodiment, the oxygen concentrator could be a small portable device capable of generating several liters of oxygen per minute.

In one embodiment, oxygen delivery system 100 also includes a flow control system 175 that control the flow, volume, and/or pressure of oxygen-enriched gas delivered from oxygen source 176 to the patient. In one embodiment, flow control system 175 includes a flow control assembly, such as a valve 175v, that controls the flow, volume, or pressure of gas/oxygen provided by source of oxygen 176 to the patient. In one embodiment, flow control system 175 may include a controller that controls flow control assembly 175v to deliver the oxygen to the patient. In one embodiment, controller is configured to implement the method of oxygen therapy according to the principles of the present patent application. In one embodiment, flow control system 175 can be implemented as a stand-alone system that attaches oxygen source 176, such as by being physically mounted onto the stem of an oxygen tank in fluid communication with the gas stored in the tank. Alternatively, in one embodiment, flow control system 175 can be provided in the same housing as oxygen source 176. If, for example, oxygen source 176 is an oxygen concentrator or a portable liquid oxygen delivery system, flow control system 175 can be provided in the same housing containing the components of the oxygen concentrator or the portable liquid oxygen delivery system.

In one embodiment, oxygen delivery system 100 also includes respiratory circuit 103. Respiratory circuit 103 is configured to deliver the pressurized flow of oxygen-enriched gas from oxygen source 176 to the airway of subject P. Respiratory circuit 103 may be configured for any of the oxygen support therapies described herein and/or other oxygen support therapies. As such, respiratory circuit 103 comprises one or more conduits 105, an interface appliance 107, and/or other components. Conduit 105 may be configured to convey the flow of oxygen-enriched gas to interface appliance 107. Interface appliance 107 may be configured to deliver the flow of oxygen-enriched gas to the airway of subject P. In some embodiments, interface appliance 107 is non-invasive. As such, interface appliance 107 non-invasively engages subject P. Non-invasive engagement comprises removably engaging an area (or areas) surrounding one or more external orifices of the airway of subject P (e.g., nostrils and/or mouth) to communicate gas between the airway of subject P and interface appliance 107. Some examples of non-invasive interface appliances may comprise, for example, a nasal cannula, a nasal mask, a nasal/oral mask, a full face mask, a total face mask, or other interface appliances that communicate a flow of oxygen-enriched gas with an airway of subject P. The present disclosure is not limited to these examples, and contemplates delivery of the flow of gas to the subject using any interface appliance.

In one embodiment, one or more sensors 106a . . . 106n includes a heart rate sensor that is configured for generating a heart rate signal, data or information indicative of the heart rate of the patient. In one embodiment, one or more sensors 106a . . . 106n includes a photoplethysmogram (PPG) sensor that is used as heart rate sensor. That is, the heart rate sensor is a PPG sensor with a sensing area. In one embodiment, the sensing area is adapted to receive a finger of the patient for measuring a PPG signal as the heart rate signal, data or information.

Although in the above described embodiments the heart rate sensor is a PPG sensor, in other embodiments, another heart rate sensor can be used. For example, electrodes can be used for measuring an electrocardiogram signal. Moreover, in one embodiment, a ballistocardiogram can be measured, for example, with a static charge sensitive bed, a piezo foil or an EMFi-film sensor build into a chair as disclosed in, for example, "An EMFi-film sensor based ballistocardiographic chair performance and cycle extraction method," S.Junnila, A. Akhbardeh, A. Varri, T. Koivistoinen; IEEE Workshop on Signal Processing Systems Design and Implementation, published 2-4 Nov. 2005, pages 373-377. Moreover, the heart rate sensor can be a unit for measuring the oxygen saturation ($SPO_2$). Furthermore, in one embodiment, instead of measuring the PPG signal, i.e., the photo-plethysmogram signal, a non-photo-plethysmogram signal can be measured. In one embodiment, the heart rate sensor can also use non-galvanic capacitive electrodes as disclosed in "High resolution ambulatory electrocardiographic monitoring using wrist-mounted electric potential sensors," C. J. Harland, T. D. Clark and R. J. Prance, Meas. Sci. Technol, volume 14, number 7, 2003, pages 923-928, a wristwatch like device as disclosed in International Patent Publication No. WO 2007/072239 A2, a seismosomnography unit as disclosed in "Contact-free measurement of heart rate, respiration rate, and body movements during sleep," M. Brink, C. H. Mueller, C. Schierz, Behavior Research Methods 2006, 38(3), pages 511-521, an ultra wide band radar, an optical vibrocardiography apparatus as disclosed in "Optical Vibrocardiography: A novel tool for the optical Monitoring of Cardiac Activity," U. Morbiducci, L. Scalise, M. delis, M. Grigioni, Annals of Biomedical Engineering, volume 35(1), pages 45-58, January 2007, an acoustical unit for acoustically sensing the heart rate via a microphone also known as phonocardiograph, etc.

In one embodiment, photoplethysmography (PPG) is a system or a method used to noninvasively measure blood volume changes during the cardiac cycle. PPG uses the change in absorption of light by tissues to measure the difference in oxygenation levels and infer the changes in blood volume.

In one embodiment, one or more sensors 106a . . . 106n includes a breathing or respiration rate sensor that is configured for generating a respiration rate signal, data or information indicative of the respiration rate of the patient.

In one embodiment, the respiratory rate is defined as the number of breaths a patient takes during a one-minute period of time. In one embodiment, the respiratory rate is measured while the patient is at rest. In one embodiment, the one or more sensors 106a . . . 106n includes a photoplethysmogram (PPG) sensor that is used as respiration rate sensor. That is, the respiration rate sensor is a PPG sensor with a sensing area. In one embodiment, the sensing area is adapted to receive a finger of the patient for measuring a PPG signal as the respiration rate signal, data or information.

Although in above described embodiments, a finger is placed at a sensing area for sensing the heart rate and/or the respiration rate, in other embodiments the heart rate and/or the respiration rate can be sensed at another part of the patient, for example, at the ear.

In one embodiment, numerous other types of sensors can be utilized. For instance, heart rate as well as respiration rate can be derived from the pressure pulse of a photoplethysmogram light emitting diodes (LED) & detectors. In one embodiment, heart rate, as well as respiration rate are also derived from electrodes in contact with the skin surface. In one embodiment, the sensors 106a . . . 106n are any type of components from which a heart rate and or respiration rate can be derived.

In one embodiment, the sensors 106a . . . 106n includes an accelerometer in order to detect activity levels and increase the accuracy of the oxygen consumption calculation.

In one embodiment, system of the present patent application provides a closed loop automatic titration of oxygen based on the determined patient's metabolic oxygen consumption rate. In one embodiment, closed loop algorithms of the present patent application rely on heart rate information/data, respiration rate information/data and accelerometer information/data provide a more robust and reliable solution.

In one embodiment, the oxygen generated would be delivered to the patient when computer system 102 acting upon information from sensors 106a . . . 106n detect an increase in the rate of metabolic oxygen consumption. In one embodiment, the increase in oxygen/air admixture begins when the information senses the beginning of an inspiration of a breath (or an end of expiration) and is turned off by the valve controller when computer system 102 detects the beginning of expiration in order to conserve oxygen by delivering the oxygen only when needed. In one embodiment, computer system 102 is configured to automatically titrates the oxygen flow delivered to the patient based on the determined metabolic oxygen consumption of the patient. In addition, studies have shown that closed loop automatic titration of oxygen improves exercise tolerance and maintain oxygen during daily activity better than constant oxygen based delivery systems.

As shown in FIGS. 1A, 1B and 2, system 100 may comprise server 102 (or multiple servers 102). Server 102 may comprise heart rate information subsystem 112, respiration rate information subsystem 114, accelerometer information subsystem 116, metabolic oxygen consumption information subsystem 118, or other components or subsystems. In one embodiment, sensors 106a . . . 106n may provide heart rate information of the patient, respiration rate information of the patient, and accelerometer information of the patient to a computer system (e.g., comprising server(s) 102) over a network (e.g., network 150) for processing. In one embodiment, sensors 106a . . . 106n may process heart rate information of the patient, respiration rate information of the patient, and accelerometer information of the patient, and provide processed information to the computer system over a network (e.g., network 150). In such embodiment, heart rate subsystem 112, respiration rate subsystem 114, and accelerometer subsystem 116 may be part of sensors 106a . . . 106n. In one embodiment, sensors 106a . . . 106n may automatically provide heart rate information of the patient, respiration rate information of the patient, and accelerometer information of the patient (e.g., obtained or processed) to the computer system (e.g., comprising server 102).

In one embodiment, heart rate subsystem 112 may obtain information associated with a patient's heart rate. In one embodiment, heart rate subsystem 112 is configured to determine the heart rate from the obtained heart rate information of the patient. That is, heart rate subsystem 112 is configured to analyze information/data from sensors 106a . . . 106n and calculate or determine heart rate based on the sensor data/information.

In one embodiment, respiration rate subsystem 114 may obtain information associated with a patient's respiration rate. In one embodiment, respiration rate subsystem 114 is configured to determine the respiration rate from the obtained respiration rate information of the patient. That is, respiration rate subsystem 114 is configured to analyze information/data from sensors 106a . . . 106n and calculate or determine respiration rate based on the sensor data/information.

In one embodiment, accelerometer subsystem 114 may obtain information associated with a patient's accelerometer value. In one embodiment, accelerometer subsystem 116 is configured to determine the accelerometer value from the obtained accelerometer information of the patient. That is, accelerometer subsystem 116 is configured to analyze information/data from sensors 106a . . . 106n and calculate or determine accelerometer value based on the sensor data/information.

In one embodiment, metabolic oxygen consumption subsystem 118 is configured to determine the metabolic oxygen consumption value from the heart rate of the patient from the heart rate subsystem 112 and the respiration rate of the patient from the respiration rate subsystem 114. In one embodiment, metabolic oxygen consumption subsystem 118 is configured to determine the metabolic oxygen consumption value from the heart rate of the patient from heart rate subsystem 112, the respiration rate of the patient from respiration rate subsystem 114 and the accelerometer value of the patient from accelerometer subsystem 116.

In one embodiment, computer system 102 is configured to determine a beginning of an inspiration of a breath of the patient and a beginning of an expiration of the patient from the respiration rate information of the patient from one or more sensors 106a . . . 106n. In one embodiment, computer system 102 is configured to increase the flow, volume, and/or pressure of the oxygen-enriched gas delivered from oxygen source 176 of oxygen delivery system 100 to patient P at the beginning of the inspiration of the breath of the patient and based on the determined metabolic oxygen consumption information of patient P. In one embodiment, computer system 102 is configured to turn off the oxygen-enriched gas delivered from oxygen source 176 of oxygen delivery system 100 to patient P at the beginning of the expiration of the patient and based on the determined metabolic oxygen consumption information of patient P.

In one embodiment, computer system 102 is configured to send or transmit signals to flow control system 175 to either increase the flow, volume, and/or pressure of the oxygen-enriched gas delivered from oxygen source 176 of oxygen delivery system 100 to patient P or turn off the oxygen-enriched gas delivered from oxygen source 176 of oxygen delivery system 100 to patient P.

In one embodiment, computer system 102 is configured to continuously adjust the flow, volume, and/or pressure of the oxygen-enriched gas delivered from oxygen source 176 of oxygen delivery system 100 to patient P based on a feedback signal generated by computer system 102. In one embodiment, the feedback signal is generated by computer system 102 such that the determined metabolic oxygen consumption information of patient P falls within a predetermined metabolic oxygen consumption range.

In one embodiment, continuous adjustment discussed in the present patent application is a feedback control. That is, the metabolic oxygen consumption is fed back to continuously adjust the flow, volume, and/or pressure of the oxygen-enriched gas delivered from oxygen source 176 of oxygen delivery system 100 to patient P based on the determined metabolic oxygen consumption information of patient P. For example, method 300 and system 100 of the present patent application continuously adjusts the flow, volume, and/or pressure of the oxygen-enriched gas delivered from oxygen source 176 of oxygen delivery system 100 to patient P based on the determined metabolic oxygen consumption information of patient P.

In one embodiment, the error term or value is derived by comparing the determined metabolic oxygen consumption information of patient P with a predetermined metabolic oxygen consumption range. In one embodiment, the error term or value includes the difference between the determined metabolic oxygen consumption information of patient P and the predetermined metabolic oxygen consumption range, if the determined metabolic oxygen consumption information of patient P falls outside the predetermined metabolic oxygen consumption range.

In one embodiment, a subsystem of system 100 may be configured to determine the predetermined metabolic oxygen consumption range using previously obtained heart rate information, previously obtained respiration rate information, previously obtained acceleration information, and/or previously determined metabolic oxygen consumption information from a plurality of patients. In one embodiment, this subsystem is also configured to continuously obtain subsequent heart rate information, subsequent respiration rate information, subsequent acceleration information and/or subsequently determined metabolic oxygen consumption information of the plurality of patients. That is, the subsystem may continuously obtain subsequent information associated with the multiple patients. As an example, the subsequent information may comprise additional information corresponding to a subsequent time (after a time corresponding to information that was used to determine the metabolic oxygen consumption information). As an example, the subsequent information may be obtained from one or more sensors. The subsequent information may be utilized to further update or modify the predetermined metabolic oxygen consumption range (e.g., new information may be used to dynamically update or modify the predetermined metabolic oxygen consumption range), etc. In one embodiment, this subsystem is configured to then continuously modify or update the predetermined metabolic oxygen consumption range based on the subsequent heart rate information, subsequent respiration rate information, subsequent acceleration information and/or subsequently determined metabolic oxygen consumption information.

In one embodiment, the predetermined metabolic oxygen consumption range may be saved into a database (e.g., database 132) and retrieved from the database as needed. As described above, the subsystem of system 100 may continuously update/modify the predetermined metabolic oxygen consumption range.

In one embodiment, computer system 102 is configured to continuously adjust the flow, volume, and/or pressure of the oxygen-enriched gas delivered from oxygen source 176 of oxygen delivery system 100 to patient P based on an increase in the determined metabolic oxygen consumption information of patient P relative to previously-determined metabolic oxygen consumption information of patient P. In one embodiment, computer system 102 is configured to send or transmit signals to flow control system 175 to continuously adjust the flow, volume, and/or pressure of the oxygen-enriched gas delivered from oxygen source 176 of oxygen delivery system 100 to patient P based on the detected increase in the metabolic oxygen consumption information of patient P. In one embodiment, previously-determined information may comprise information corresponding to a previous time (before a time corresponding to information that was used to determine the metabolic oxygen consumption information).

In one embodiment, oxygen delivery system 100 also comprises oxygen delivery flow path, a user interface, and/or other components. In one embodiment, user interface is configured to provide an interface between oxygen delivery system 100 and the patient. In one embodiment, the heart rate information of the patient, the acceleration information of the patient, the respiration rate information of the patient, the determined metabolic oxygen consumption information of the patient and/or other information may be displayed to the patient via user interface. In one embodiment, the patient may specify one or more oxygen therapy regimes that are to be delivered to the patient using the user interface. Examples of interface devices suitable for inclusion in the user interface comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface comprises a plurality of separate interfaces. In one embodiment, user interface comprises at least one interface that is provided integrally with system 100.

Figure 3:
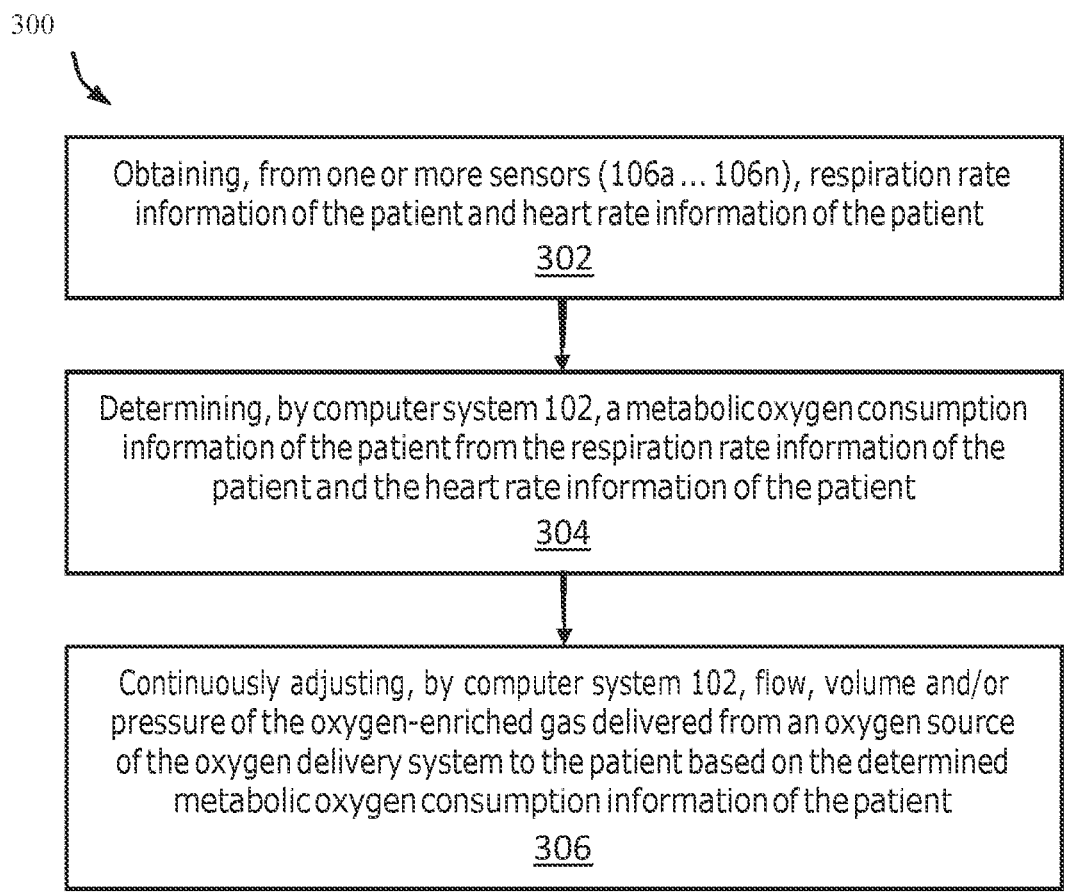
FIG. 3 shows a method for providing controlled flow of oxygen-enriched gas to a patient in accordance with an embodiment of the present patent application.

FIG. 3 is a flow chart for providing controlled flow of oxygen-enriched gas from oxygen delivery system 100 to patient P. Referring to FIG. 3, a method 300 for providing controlled flow of oxygen-enriched gas from oxygen delivery system 100 to patient P is implemented by computer system 102. In one embodiment, computer system 102 comprises one or more physical processors operatively connected to one or more sensors 106*a* . . . 106*n* and executing computer program instructions which, when executed, perform method 300. Method 300 comprises: obtaining, from one or more sensors (106*a* . . . 106*n*), respiration rate information of the patient and heart rate information of the patient at procedure 302; determining, by computer system 102, a metabolic oxygen consumption information of the patient from the respiration rate information of the patient and the heart rate information of the patient at procedure 304; and continuously adjusting, by computer system 102, flow, volume and/or pressure of the oxygen-enriched gas delivered from an oxygen source of the oxygen delivery system to the patient based on the determined metabolic oxygen consumption information of the patient at procedure 306.

Thus, in one embodiment, system 100 and method 300 of the present patent application are configured to determine patient's metabolic oxygen consumption value. In one embodiment, system 100 and method 300 of the present patent application are configured to control the flow, volume, or pressure of gas from oxygen delivery system 100 based on the determined of a patient's metabolic oxygen consumption rate.

In one embodiment, Applicant of the present patent application has found that adjusting the delivery of an oxygen-air admixture to the patient based on the determined metabolic oxygen consumption is a more proactive method than controlling the flow of oxygen either continuous/pulsed or closed-loop based on the oxygen saturation ($SpO_2$) alone. It is analogous to knowing the amount of fuel in your car's gas tank, but not your miles per gallons. In one embodiment, an effective closed loop system may increase oxygenation, provide better oxygen utilization and, therefore, increase patient mobility and activity levels. In one embodiment, an oxygen consumption indicator acts like a miles per hour gauge, and through correlation provides a user an estimate of "time to empty" for bottled oxygen systems or a "time to battery depletion" for portable oxygen concentrator system, thus allowing a person/patient to time their activity level by informing them of their ambulatory time left.

In one embodiment, system 100 of the present patent application may be incorporated into an oxygen delivery system provides significant advantages and market differentiation by constantly supporting the oxygen patient versus continuous flow and pulse dose flow systems.

In one embodiment, an additional benefit is oxygen conservation where oxygen delivery or production can be throttled based on a person's or patient's demand. In one embodiment, new clinical evidence suggests hyperoxia (excessive oxygen) may have deleterious effects on patients. So, conservative oxygen therapy represents the treatment of choice to avoid exposure to both hypoxaemia and excess hyperoxaemia. For example, João Carlos Winck, in a recent edition (2017) of the European Respiratory Journal {*Intelligent oxygen delivery in the acute setting: "Don't think twice, it's all right"*; João Carlos Winck; European Respiratory Journal 2017 50: 1701013; DOI: 10.1183/13993003.01013-2017, incorporated by reference in its entirety into the present patent application} states that oxygen therapy should be considered like a drug prescription and so careful titration should be tightly controlled. Therefore, targeted oxygen therapy, as provided by system 100 and method 300 of the present patent application, may result in the reduction of its potential side effects.

In one embodiment, system 100 and method 300 of the present patent application may be used for patients with impaired pulmonary function that require prescription oxygen delivery devices, either by bottled gas or portable oxygen concentrators that experience periods when they are hypoxic.

In one embodiment, according to the American Lung Association, "oxygen therapy is needed in COPD when lung function is reduced to such a degree that it interferes with normal bodily functions and the ability to maintain or increase activity." Hypoxemia occurs more frequently when a patient is active, that is, when their heart rate and respiration rate increases. In one embodiment, system 100 and method 300 of the present patent application may be used for COPD patients that need oxygen therapy. In one embodiment, system 100 and method 300 of the present patent application may be used for patients that experience Hypoxemia. In one embodiment, system 100 and method 300 of the present patent application may be used for Chronic Heart Failure (CHF) patients that need oxygen therapy.

In some embodiments, the various computers and subsystems illustrated in FIG. 2 may comprise one or more computing devices that are programmed to perform the functions described herein. The computing devices may include one or more electronic storages (e.g., database 132, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, or a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-118 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-118 described herein is for illustrative purposes, and is not intended to be limiting, as any of subsystems 112-118 may provide more or less functionality than is described. For example, one or more of subsystems 112-118 may be eliminated, and some or all of its functionality may be provided by other ones of subsystems 112-118. As another example, additional subsystems may be programmed to perform some or all of the functionality attributed herein to one of subsystems 112-118.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A non-invasive oxygen delivery system comprising:
   an oxygen source configured for non-invasive oxygen-enriched gas delivery to a patient;
   one or more sensors configured to generate output signals conveying information related to respiration rate, heart rate, and activity level of the patient; and
   a computer system that comprises one or more physical processors operatively connected with the oxygen source and the one or more sensors, the one or more physical processors being programmed with computer program instructions which, when executed cause the computer system to:
   determine respiration rate information of the patient, heart rate information of the patient, and activity level of the patient;
   determine metabolic oxygen consumption information of the patient from the respiration rate information of the patient and the heart rate information of the patient; and
   continuously adjust flow, volume, and/or pressure of the oxygen-enriched gas delivered from the oxygen source to the patient based on the determined metabolic oxygen consumption information of the patient and the activity level of the patient.

2. The system of claim 1, wherein the one or more sensors are further configured to generate output signals conveying information related to acceleration information of the patient and wherein the computer system is configured to determine the metabolic oxygen consumption information of the patient from the respiration rate information of the patient, the heart rate information of the patient and the acceleration information of the patient.

3. The system of claim 1, wherein the computer system is configured to determine a beginning of an inspiration of a breath of the patient and a beginning of an expiration of the patient from the respiration rate information of the patient from the one or more sensors, and wherein the computer system is configured to increase the flow, volume, and/or pressure of the oxygen-enriched gas delivered from the oxygen source of the oxygen delivery system to the patient at the beginning of the inspiration of the breath of the patient and based on the determined metabolic oxygen consumption information of the patient and turn off the oxygen-enriched gas delivered from the oxygen source of the oxygen delivery system to the patient at the beginning of the expiration of the patient and based on the determined metabolic oxygen consumption information of the patient.

4. The system of claim 1, wherein the computer system is configured to continuously adjust the flow, volume, and/or pressure of the oxygen-enriched gas delivered from the oxygen source of the oxygen delivery system to the patient based on a feedback signal generated by the computer system, wherein the feedback signal is generated such that the determined metabolic oxygen consumption information of the patient falls within a predetermined metabolic oxygen consumption range.

5. The system of claim 1, wherein the computer system is configured to increase the flow, volume, and/or pressure of the oxygen-enriched gas delivered from the oxygen source of the oxygen delivery system to the patient based on an increase in the determined metabolic oxygen consumption information of the patient relative to a previously-determined metabolic oxygen consumption information of the patient.

6. The system of claim 1, wherein the one or more physical processors are configured to estimate an amount of time before the oxygen source is empty based on the determined metabolic oxygen consumption information and the level of activity of the patient.

7. The system of claim 1, wherein the non-invasive oxygen delivery system comprises an oxygen consumption indicator configured to provide an indication of the estimated time left before the oxygen source is empty.

8. A method for non-invasive oxygen delivery to a patient using a non-invasive oxygen delivery system, the method comprising:
   delivering, with an oxygen source coupled to a non-invasive user interface, oxygen-enriched gas to the patient;
   generating, with one or more sensors, output signals conveying information related to respiration rate, heart rate, and activity level of the patient;
   determining, with one or more processors, respiration rate information of the patient, heart rate information of the patient, and activity level of the patient based on the output signals;
   determining, with the one or more processors, metabolic oxygen consumption information of the patient from the respiration rate information of the patient and the heart rate information of the patient, the metabolic oxygen consumption being an amount of oxygen taken up and utilized by the patient's body; and
   continuously adjusting, with the one or more processors, flow, volume and/or pressure of the oxygen-enriched gas delivered to the patient based on the determined metabolic oxygen consumption information of the patient and the activity level of the patient.

9. The method of claim 8, further comprising:
   generating, with the one or more sensors, acceleration information of the patient; and
   determining, with the one or more processors, the metabolic oxygen consumption information of the patient from the respiration rate information of the patient, the heart rate information of the patient and the acceleration information of the patient.

10. The method of claim 8, further comprising:
    determining, with the one or more processors, a beginning of an inspiration of a breath of the patient and a beginning of an expiration of the patient from the respiration rate information of the patient from the one or more sensors, increasing, with the one or more processors, the flow, volume, and/or pressure of the oxygen-enriched gas delivered from the oxygen source of the oxygen delivery system to the patient at the beginning of the inspiration of the breath of the patient and based on the determined metabolic oxygen consumption information of the patient and turning off the oxygen-enriched gas delivered from the oxygen source of the oxygen delivery system to the patient at the beginning of the expiration of the patient and based on the determined metabolic oxygen consumption information of the patient.

11. The method of claim 8, further comprising:

continuously, with the one or more processors, adjusting the flow, volume, and/or pressure of the oxygen-enriched gas delivered from the oxygen source of the oxygen delivery system to the patient based on a feedback signal generated by the one or more processors, wherein the feedback signal is generated such that the determined metabolic oxygen consumption information of the patient falls within a predetermined metabolic oxygen consumption range.

12. The method of claim 8, further comprising:

continuously adjusting, with the one or more processors, the flow, volume, and/or pressure of the oxygen-enriched gas delivered from the oxygen source of the oxygen delivery system to the patient based on an increase in the determined metabolic oxygen consumption information of the patient relative to a previously determined metabolic oxygen consumption information of the patient.

13. The method of claim 8, further comprising:

estimating, with the one or more processors, an amount of time before the oxygen source is empty based on the determined metabolic oxygen consumption information and the level of activity of the patient.

14. The method of claim 8, further comprising:

providing, with an oxygen consumption indicator, an indication of the estimated time left before the oxygen source is empty.

15. A non-invasive oxygen delivery system, the system comprising:

means for non-invasively delivering, with an oxygen source, oxygen-enriched gas to a patient;

means for generating output signals conveying information related to respiration rate, heart rate, and activity level of the patient;

means for determining respiration rate information of the patient, heart rate information, and activity level of the patient;

means for determining metabolic oxygen consumption information of the patient from the respiration rate information of the patient and the heart rate information of the patient, the metabolic oxygen consumption being an amount of oxygen taken up and utilized by the patient's body; and means for continuously adjusting flow, volume and/or pressure of the oxygen-enriched gas delivered to the patient based on the determined metabolic oxygen consumption information of the patient and the activity level of the patient.

16. The system of claim 15, further comprising:

means for measuring acceleration information of the patient; and means for determining the metabolic oxygen consumption information of the patient from the respiration rate information of the patient, the heart rate information of the patient and the acceleration information of the patient.

17. The system of claim 15, further comprising:

means for determining a beginning of an inspiration of a breath of the patient and a beginning of an expiration of the patient from the respiration rate information of the patient from the one or more sensors;

means for increasing the flow, volume, and/or pressure of the oxygen-enriched gas delivered from the oxygen source of the oxygen delivery system to the patient at the beginning of the inspiration of the breath of the patient and based on the determined metabolic oxygen consumption information of the patient; and means for turning off the oxygen-enriched gas delivered to the patient at the beginning of the expiration of the patient and based on the determined metabolic oxygen consumption information of the patient.

18. The system of claim 15, further comprising:

means for continuously adjusting the flow, volume, and/or pressure of the oxygen-enriched gas delivered from the oxygen source of the oxygen delivery system to the patient based on a feedback signal generated by the computer system, wherein the feedback signal is generated such that the determined metabolic oxygen consumption information of the patient falls within a predetermined metabolic oxygen consumption range.

19. The system of claim 15, further comprising:

means for continuously adjusting the flow, volume, and/or pressure of the oxygen-enriched gas delivered to the patient based on an increase in the determined metabolic oxygen consumption information of the patient relative to a previously determined metabolic oxygen consumption information of the patient.

20. The system of claim 15, further comprising:

means for estimating an amount of time before the oxygen source is empty based on the determined metabolic oxygen consumption information and the level of activity of the patient; and means for providing, with an oxygen consumption indicator, an indication of the estimated time left before the oxygen source is empty.

* * * * *